(12) United States Patent
Hirth et al.

(10) Patent No.: US 7,968,704 B2
(45) Date of Patent: Jun. 28, 2011

(54) PROCESS FOR THE PRODUCTION OF SUGAR ALCOHOLS

(75) Inventors: Thomas Hirth, Bühl (DE); Rainer Schweppe, Karlsruhe (DE); Jürgen Graf, Pfinztal (DE); Rainer Busch, Baden-Baden (DE); Matthias Pursch, Rheinmünster (DE)

(73) Assignee: Fraunhofer-Gesellschaft zur Förderung der angewandten Forschung e.V., München (DE)

( * ) Notice: Subject to any disclaimer, the term of this patent is extended or adjusted under 35 U.S.C. 154(b) by 651 days.

(21) Appl. No.: 11/792,245

(22) PCT Filed: Dec. 7, 2005

(86) PCT No.: PCT/EP2005/013085
§ 371 (c)(1),
(2), (4) Date: Jun. 4, 2007

(87) PCT Pub. No.: WO2006/061196
PCT Pub. Date: Jun. 15, 2006

(65) Prior Publication Data
US 2008/0051573 A1    Feb. 28, 2008

(30) Foreign Application Priority Data
Dec. 7, 2004 (DE) .......... 10 2004 058 811

(51) Int. Cl.
 C07H 1/00 (2006.01)
 C07H 3/00 (2006.01)
 C08B 37/00 (2006.01)
(52) U.S. Cl. ..................................... 536/124
(58) Field of Classification Search .......... None
See application file for complete search history.

(56) References Cited

U.S. PATENT DOCUMENTS

| | | | |
|---|---|---|---|
| 3,055,840 A | 9/1962 | Koch | |
| 3,935,284 A * | 1/1976 | Kruse | ............ 568/863 |
| 4,380,680 A | 4/1983 | Arena | |
| 4,413,152 A | 11/1983 | Arena | |
| 4,471,144 A | 9/1984 | Arena | |
| 4,487,980 A | 12/1984 | Arena | |
| 4,520,211 A | 5/1985 | Lepper | |
| 5,601,863 A * | 2/1997 | Borden et al. | ............ 426/548 |
| 6,235,797 B1 | 5/2001 | Douglas | |
| 2002/0133048 A1 | 9/2002 | Douglas | |

FOREIGN PATENT DOCUMENTS

| | | |
|---|---|---|
| DE | 1 931 112 | 1/1970 |
| DE | 102 58 089 | 6/2004 |
| EP | 0 773 063 | 5/1997 |
| GB | 806 236 | 12/1958 |
| WO | WO 2005/021475 | 3/2005 |

OTHER PUBLICATIONS

Arena: "Deactivation of ruthenium catalysts in continuous glucose hydrogenation". Appl. Catal. A. vol. 87, 1992, Pa. 219-229.
Gallezot P et al: "Glucose Hydrogenation on Ruthenium Catalysts in a Trickle-Bed Reactor". Journal of Catalysis, Academic Press, Duluth, MN, US, vol. 180, Nr. 1, Pa. 51-55, 1998.
Kusserow et al: "Hydrogenation of Glucose to Sorbitol over Nickel and Ruthenium Catalysts". Adv. Synth. Catal., vol. 345, Nr. 1/2, Pa. 289-299, 2003.

* cited by examiner

Primary Examiner — Layla Bland
(74) Attorney, Agent, or Firm — Paul Vincent

(57) ABSTRACT

Disclosed is a method for producing polyalcohols in the form of sugar alcohols from the group comprising sorbitol and mannitol and other optional $C_2$ to $C_6$ polyols. According to said method, a monosaccharide, disaccharide, oligosaccharide, or polysaccharide containing at least one glucose unit and/or at least one fructose unit is continuously reacted with hydrogen at an elevated temperature and at a great pressure in an aqueous phase in the presence of a hydrogenating catalyst based on ruthenium or ruthenium oxide so as to obtain the inventive polyalcohols. The minimum temperature is set at 100° C. while the minimum pressure is set at 150 bar and the maximum dwell time of the reactants during catalytic hydrogenation is set at 600 s. The inventive method is particularly suitable for producing the sugar alcohols sorbitol and/or mannitol or $C_2$ to $C_6$ polyols from glucose, fructose, or disaccharides, oligosaccharides, or polysaccharides containing glucose units or fructose units, especially saccharose, practically all the used saccharides being reacted without turning into caramel. Furthermore, the yield of said sugar alcohols or $C_2$ to $C_6$ polyols is exceptionally high while the selectivity for the desired products can be varied in a simple manner within broad boundaries.

11 Claims, 1 Drawing Sheet

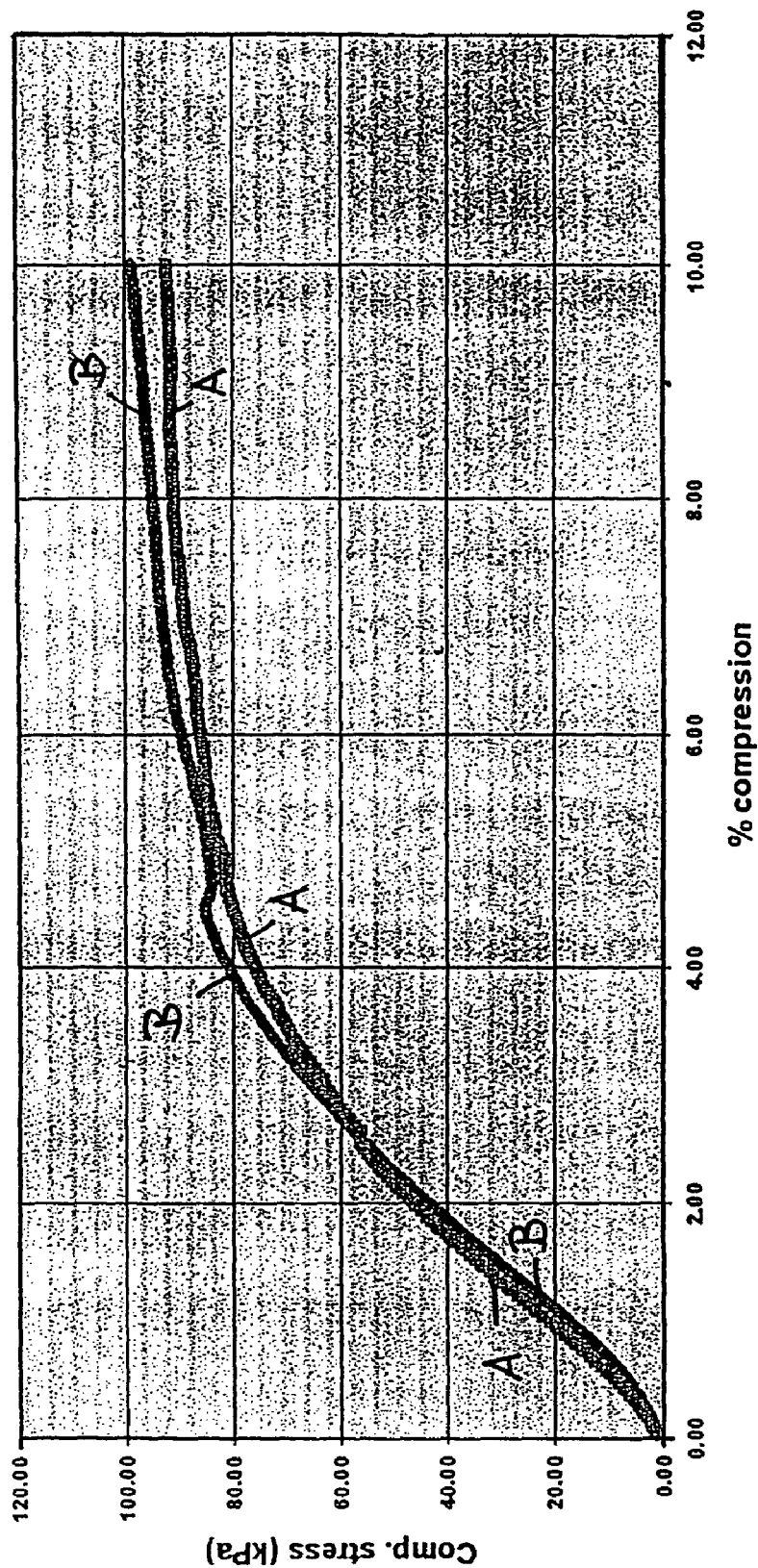

US 7,968,704 B2

PROCESS FOR THE PRODUCTION OF SUGAR ALCOHOLS

This application is the national stage of PCT/EP2005/013085 filed on Dec. 7, 2005 and also claims Paris Convention priority of DE 10 2004 058 811.2 filed Dec. 7, 2004.

BACKGROUND OF THE INVENTION

The invention relates to a process for the production of polyalcohols in the form of sugar alcohols from the group of sorbitol and/or mannitol and optionally further $C_6$ and/or C4 and/or $C_3$ and/or $C_2$ polyols.

Sugar alcohols have numerous industrial uses. Thus, e.g. sorbitol is in particular used as a sugar substitute with a sweetening character, e.g. for dietetic foods, in the cosmetic and pharmaceutical industries and also technically in the paper and textile industries. Mannitol is e.g. also used as a sugar substitute, as a filler in the pharmaceutical industry, in the production of synthetic resins, etc. In addition, polyols with up to six carbon atoms, such as propanediols, propanetriols (glycerin) and butanediols are of great technical significance and are e.g. used in the petrochemical industry as a base substance for the production of plastics. At present such polyols are obtained from fossil fuels, particularly petroleum and after fractionation are used for plastic synthesis, such as in the production of polyurethanes. In this connection the term "polyols" also covers organic alcohols with at least two hydroxy groups.

For the production of sugar alcohols biochemical processes are known, in which sugar alcohols are produced by enzymatic treatment of the corresponding monosaccharides, but this requires very long reaction times lasting several hours or days in order to obtain a high sugar alcohol yield.

Thus, sugar alcohols are generally produced by the catalytic hydrogenation of saccharides or other carbonyl compounds with hydrogen under elevated pressure and temperature. Apart from discontinuous or batchwise performed processes in which the reaction mixture is generally stirred over several hours, continuous processes are known in which the reaction mixture is contacted in tubular reactors with the hydrogenating catalyst.

DE 1 002 304 A describes a process for the continuous hydrogenation of reducible sugars, where a fine particular nickel catalyst is suspended, mixed with an aqueous educt solution and then the mixture is continuously contacted under elevated pressure and temperature with a hydrogen flow. The educts used are in particular glucose, inverted cane sugar or lactose, which have been reacted in the aforementioned manner to sorbitol and mannitol (from glucose or inverted cane sugar) or lactosite (from lactose). However, the long reaction times necessary for a satisfactory conversion yield and the relatively limited selectivity for the production of the specific sugar alcohols are disadvantageous.

DE 960 352 B discloses a process for the production of a mixture of the sugar alcohols sorbitol and mannitol, in that an aqueous saccharose solution is hydrolyzed under elevated pressure and temperature in the presence of a nickel catalyst. However, it is disadvantageous that there is a long reaction time of 45 minutes up to several hours necessary in order to achieve a satisfactory hydrolysis reaction yield, the latter being broken off when it is completed in a range between 95% and 99%. Furthermore the selectivity with respect to specific representatives of sugar alcohols is relatively limited.

DE 199 29 368 A1 describes a process for the production of the sugar alcohol mannitol from fructose, the fructose being continuously hydrogenated in the presence of a Raney nickel catalyst at a temperature between 50° and 180° C. and a pressure between 50 and 300 bar. Fructose is used in aqueous solution and hydrogen is used as the hydrogenating agent. No information is given on the reaction time necessary for a satisfactory educt reaction, but here again the selectivity is relatively limited and in particular exclusively mannitol and sorbitol mixtures can be produced.

DE 100 65 029 A1 relates to a similar process for the production of alcohols, particularly sugar alcohols, by reacting carbonyl compounds, particularly sugars, such as sorbitol from dextrose, sorbitol and mannitol from fructose, xylite from xylose, maltite from maltose, isomaltite from isomaltose, dulcite from galactose and lactite from lactose. The educts are continuously reacted with hydrogen in the presence of a Raney catalyst based on nickel, cobalt, copper, iron, platinum, platinum, palladium or ruthenium in aqueous solution. A pressure between 30 and 450 bar and a temperature of max. 150° C. are set, in order in the case of the use of sugars as educts to ensure that the latter do not caramelize. With regards to the production of sugar alcohols, no details are given on the reaction time or selectivity and as a result of the indicated caramelization risk at temperatures above 150° C. and a multistage hydrogenation relatively long reaction times must be assumed.

DE 1 931 112 A1 describes a process for the production of mannitol and sorbitol from saccharose, in that a saccharose solution is hydrogenated with hydrogen in the presence of a hydrogenating catalyst at a temperature of approximately 160° to 190° C. and a pressure of approximately 35 to 211 bar, the process being continuously performable. Metal catalysts based on nickel are referred to as hydrogenating catalysts. The residence time is 15 minutes to 2.5 hours.

EP 773 063 A1 discloses another process for hydrogenating pure sugar alcohols using a hydrogenating catalyst in the form of Raney nickel. The process parameters indicated are e.g. temperatures of 110° to 150° C. and pressures of 40 to 200 bar. According to an embodiment crystalline glucose is hydrogenated at 130° C. and 150 bar in a continuous Raney nickel flow through a reactor, the sorbitol yield obtained being 99.3%. The use of a catalyst based on ruthenium/ruthenium oxide is not mentioned, because when performing the process in accordance with EP 773 063 A1 this allegedly leads to isomerization, decomposition and polymerization during hydrolysis.

The problem of the invention is to further develop a process for the production of polyalcohols of the aforementioned type in such a way that in the case of a high selectivity for the desired sugar alcohols, particularly sorbitol and/or mannitol, as well as optionally for further $C_2$ to $C_6$ polyols, it is economic and effective and in particular permits a simple control of the selectivity with respect to the in each case desired products.

SUMMARY OF THE INVENTION

In the case of a process of the aforementioned type, the invention solves this problem in that at least one mono-, di-, oligo- and/or polysaccharide containing a glucose and/or at least one fructose unit is continuously reacted in the presence of a hydrogenating catalyst based on ruthenium (Ru) and/or ruthenium oxide in aqueous phase, at elevated temperature and elevated pressure, with hydrogen and accompanied by the obtaining of the indicated polyalcohols, a temperature of at least 100° C., a pressure of at least 150 bar and a residence time of the reactants during catalytic hydrogenation of max. 600 s being set.

It has surprisingly been found that with such a very short residence time, i.e. in the case of a very short contact time of the indicated educts in the aqueous phase with the hydrogen in the presence of the hydrogenating catalyst based on ruthenium/ruthenium oxide of max. 600 s, preferably max. 500 s, more particularly max. 400 s, it is possible to obtain a substantially complete conversion of the educts, without any caramelization or other deterioration thereof even at a temperature in the range of or above approximately 150° C. In particularly preferred manner, the residence time is between approximately 5 s and approximately 360 s, e.g. in the range approximately 180 to approximately 240 s.

According to the invention and as a function of the desired product range, the educt used is at least one mono-, di-, oligo- and/or polysaccharide containing at least one glucose and/or fructose unit, e.g. preferably glucose and/or fructose. It is also possible to use e.g. di-, oligo- and/or polysaccharides containing at least one glucose and/or fructose unit. With the latter alternative it can be advantageous to use a di-, oligo- and/or polysaccharide containing at least one glucose unit and also at least one fructose unit, more particularly saccharose (glucose-fructose) and/or raffinose (glucose-fructose-galactose).

As will be explained hereinafter, if such an educt (e.g. glucose) is used, in the case of an appropriate control of the process parameters it is possible to obtain a selectivity of the product (e.g. sorbitol) of almost 100% and in particular through varying the temperature, pressure, short residence time and/or hydrogen/educt concentration, the selectivity for other possible products (e.g. mannitol or shorter-chain polyalcohols) can be controlled in a planned manner.

With the inventively used catalysts based on ruthenium (Ru) and/or ruthenium oxide, with the indicated, short residence times it is possible to obtain an almost complete conversion of a glucose and/or fructose-containing educt with a (as a function of the temperature and/or pressure, short residence time and/or hydrogen/educt concentration) very high selectivity of sorbitol and/or mannitol and/or shorter-chain polyols. Said catalysts based on ruthenium (Ru) and/or ruthenium oxide with regards to a complete educt conversion and an extremely high selectivity with respect to the indicated products, have proved surprisingly superior to other known hydrogenating catalysts. Mixed catalysts have proved advantageous, which contain both ruthenium and ruthenium oxide and which are preferably immobilized on at least one carrier, such as aluminium oxide ($Al_2O_3$). A further advantage of such catalysts based on ruthenium or ruthenium oxide, e.g. compared with catalysts based on Raney nickel widely used for the production of sugar alcohols, is that their activity is maintained over a very long time period, they are not toxic and consequently can be easily handled.

With regards to the pressure during the continuous hydrogenation reaction, a pressure of at least 200 bar and preferably at least 220 bar has proved advantageous. Particular preference is given to values between approximately 220 and approximately 280 bar, particularly between approximately 230 and approximately 270 bar, e.g. around 250 bar.

Preferably a temperature between 100° and 300° C., especially between 120° and 280° C. is set and, e.g. in the case of the production of sorbitol from glucose or sorbitol and mannitol from fructose the temperature is preferably set in the range between approximately 120° and approximately 180° C., particularly between approximately 130° and approximately 170° C., e.g. around 150° C. Particularly when using an educt in the form of glucose, it is possible to obtain a selectivity for sorbitol of almost 100° C. with a virtually complete educt conversion. However, if interest is attached to obtaining a higher proportion of mannitol from glucose, the temperature is preferably increased to approximately 280° C., particularly up to approximately 250° C., e.g. up to approximately 225° C., in order to increase the selectivity for mannitol compared with that for sorbitol. When using di-, oligo- and/or polysaccharides, such as e.g. a disaccharide from a glucose unit and a fructose unit (saccharose) or a trisaccharide from a glucose, a fructose and a galactose unit (raffinose), then the preferred temperature range is approximately 175° to 225° C., preferably approximately 200° C., in order to initially completely split the educt used. On increasing the temperature to approximately 225° C. or higher, the selectivity of the inventive process can be shifted towards the $C_2$, $C_3$, $C_4$ and/or $C_6$ polyols, such as in particular 1,3-propanediol, glycerin (1,2,3-propanetriol), 2,3-butanediol, 1,4-butanediol, 1,2-ethanediol and optionally further partially hydrogenated sugar alcohols in smaller quantities.

BRIEF DESCRIPTION OF THE DRAWING

The sole drawing shows a preferred embodiment in accordance with the invention.

DESCRIPTION OF THE PREFERRED EMBODIMENT

Thus, as has already been stated, the inventive process offers the possibility to adjust the product proportions of the sugar alcohols sorbitol and mannitol or the indicated polyalcohols by varying at least one of the parameters temperature, particularly in a range between 120° and 280° C. or the aforementioned, preferred temperature ranges, pressure, residence time and/or hydrogen or educt concentration. Thus, in this way the selectivity can be controlled with a substantially complete educt conversion between approximately 100% for sorbitol, via a preponderant mannitol proportion up to shorter-chain polyalcohols, such as e.g. 1,3-propanediol, propanetriol (glycerin), 2,3-butanediol, 1,4-butanediol and ethanediol. With regards to the latter polyalcohols, it has been surprisingly found that through the inventive process product ranges for such alcohols can be obtained, which in the production of polyurethanes directly from the mixture obtained can give better results than when producing, in accordance with the prior art of polyurethanes from the corresponding product range obtained from petroleum. Thus, the graph shown in the attached drawing, reveals that the compressive stress ("comp stress" in [kPa]) in polyurethanes (curve A), produced directly by polymerization from polyols produced using the process of the invention (experiment E9 in example 3 hereinafter), as a function of the pressure ("compression" in [%]) is lower than in polyurethanes (curve B), which have been produced directly by polymerization of a commercial petroleum product containing the corresponding polyols.

Particularly for the production of sorbitol and/or mannitol, an educt concentration e.g. for the educt glucose, of between 5 and 50 mass %, particularly between 10 and 40 mass %, based on the total flow, i.e. educt including the solvent water, has proved advantageous. However, a different educt concentration can be chosen, e.g. particularly lower than 5 mass %, mainly if the other polyalcohols are to be produced.

Hereinafter the inventive process is further explained relative to embodiments, in which (tables 2, 4, 6, 8, 10, 12 and 14) the following meanings are used:

($^1$ TOC: Total Organic Carbon ($^2$ Yield: In each case for an educt conversion (here glucose or fructose or saccharose) of 100%, i.e. the yield corresponds to the selectivity—all the yields are mass-specific taking account of the higher molecular weight of the hydrogenated product compared with the educt.

Example 1

Continuous production of the sugar alcohols sorbitol and/or mannitol and optionally further polyalcohols by hydrogenating glucose in aqueous solution with gaseous hydrogen in the presence of a ruthenium/ruthenium oxide mixed catalyst on aluminium oxide in the form of a fixed bed introduced into the reactor.

The monosaccharide glucose as the educt is continuously reacted in aqueous solution with gaseous hydrogen in a high quality steel tubular reactor with a length of twice 163 cm (connected in parallel) and an internal diameter of 9 mm. There is a fixed bed of a ruthenium/ruthenium oxide mixed catalyst on particles of aluminium oxide as the carrier in the tubular reactor. The experiment is performed four times, i.e. in each case twice at 150° C. and twice at 200° C., the parameters given in the following table 1 being set.

TABLE 1

| Experiment | E1 | E2 | E3 | E4 |
|---|---|---|---|---|
| Glucose concentration of solution used (mass % glucose in aqueous solution) | 30 | 30 | 30 | 30 |
| Glucose concentration in reactor (mass % glucose in total reactor mass flow) | 5 | 5 | 20 | 20 |
| Hydrogen concentration used (mole $H_2$ per mole of glucose used) | 100 | 100 | 25 | 25 |
| Residence time in reactor (seconds, s) | 300 | 300 | 300 | 300 |
| Temperature in reactor (° C.) | 200 | 200 | 150 | 150 |
| Pressure in reactor (bar) | 250 | 250 | 250 | 250 |
| Mass flows in reactor: | | | | |
| a) total mass flow [kg/h] | 0.946 | 0.946 | 0.998 | 0.998 |
| b) water mass flow [ml/min] | 12.612 | 12.612 | 5.074 | 5.074 |
| c) 30% glucose mass flow [ml/min] | 2.368 | 2.368 | 9.996 | 9.996 |
| d) hydrogen mass flow [ml/min] | 29.166 | 29.166 | 30.786 | 30.786 |
| pH-Value | 6 | 6 | 6 | 6 |

For performing experiments E1 to E4 the reactor with the hydrogenating catalyst contained therein in the form of a fixed bed is initially started up, in that the reactor is subject to a clean water flow at the reaction pressure of 250 bar and reaction temperature of 150° or 200° C. On reaching a constant water flow under the indicated pressure and temperature conditions, a hydrogen flow is supplied to the reactor in order to reduce and therefore activate the hydrogenating catalyst. On setting a constant water flow and constant hydrogen flow with the value given in table 1, the 30% glucose solution is added and the glucose mass flow indicated in table 1 is set. In the present embodiment the glucose concentration in the reactor is so set by means of dosing pumps that there is a value of 5 (experiments E1 and E2) or 20 mass % (experiments E3 and E4), based on the total mass flow added to the reactor. The residence time of 300 s or 5 min can also be set by corresponding control of the associated dosing pump, whilst taking account of the density of the medium under the conditions prevailing in the reactor and the given volume flow.

The following table 2 gives the results obtained in the experiments based on the conversion of the glucose used as the educt and the yields of the sugar alcohols sorbitol, mannitol and further polyalcohols obtained as products.

TABLE 2

| Experiment | E1 | E2 | E3 | E4 |
|---|---|---|---|---|
| Carbon recovery rate ($TOC_{products}$[1]/$TOC_{educts}$[1] in [%]) | 89 | 83 | 96 | 97 |
| Glucose conversion [%] | 100 | 100 | 100 | 100 |
| Sorbitol yield[2] [%] | 45 | 62 | 98 | 98 |
| Mannitol yield[2] [%] | 21 | 13 | <1.5 | <1.5 |
| $C_6$-alcohol yield [%] | 13 | 8 | <0.5 | <0.5 |
| $C_3$-/$C_4$-alcohol yield [%] | 13 | 8 | 0 | 0 |

Experiments E1 to E4 show that with a residence time of 300 s, a pressure of 250 bar and a temperature of 150° C. it is possible to bring about a complete glucose conversion of 100% during the continuous catalytic hydrogenation of glucose with hydrogen in the presence of ruthenium/ruthenium oxide on aluminium oxide. There is an extremely high yield/selectivity of the sugar alcohol sorbitol of 98%, whereas for the sugar alcohol mannitol there is a low yield/selectivity of max. 1.5%. As further reaction products it was only possible to detect other $C_6$ alcohols in extremely small proportions of max. 0.5%.

As can also be seen, the yield of the sugar alcohol mannitol and further polyols, particularly $C_3$ and $C_4$ polyalcohols, compared with sorbitol can be increased in that the temperature is raised to a value higher than about 150° C., here 200° C. There is a sorbitol to mannitol product ratio between approximately 1:2 and approximately 1:3, without any caramelization of the glucose used due to the inventively very short residence time in the reactor. With such a temperature rise to 200° C., further $C_3$, $C_4$ and $C_6$ alcohols with a total proportion of approximately 20% are obtained. The proportion of $C_3$ and $C_4$ polyalcohols is approximately 10%, based on the total product quantity and consists almost exclusively of the $C_3$ polyalcohol 1,3-propanediol and the $C_4$-polyalcohols 2,3-butanediol and 1,4-butanediol. There is also a complete conversion of the glucose used of 100% at this temperature.

As is apparent from the following example 2, the yield of shorter-chain alcohols increases with rising temperature due to thermal decomposition and on producing sorbitol from glucose optimum process parameters are a pressure of approximately 250 bar, a temperature of approximately 150° C. and a residence time of approximately 300 s. An advantageous hydrogen concentration is between 10 and 200 mole hydrogen/mole of glucose used, preferably between approximately 20 and 150 mole hydrogen/mole of glucose used.

Example 2

Continuous production of the sugar alcohols sorbitol and mannitol, as well as further polyalcohols by hydrogenating glucose in aqueous solution with gaseous hydrogen in the presence of a ruthenium/ruthenium oxide mixed catalyst on aluminium oxide in the form of a fixed bed introduced into the reactor.

The monosaccharide glucose as the educt is continuously reacted in aqueous solution with gaseous hydrogen in a high quality steel tubular reactor with a length of twice 163 cm (connected in parallel) having an internal diameter of 9 mm in accordance with example 1. The tubular reactor contains a fixed bed of a ruthenium/ruthenium oxide mixed catalyst on particles of aluminium oxide as the carrier. The experiment is performed at higher temperatures than in example 1, namely once at 225° C. and once at 250° C., the parameters given in table 3 being set.

TABLE 3

| Experiment | E5 | E6 |
|---|---|---|
| Glucose concentration of solution used [mass.-% glucose in aqueous solution] | 30 | 30 |
| Glucose concentration in reactor [mass.-% glucose in total reactor mass flow] | 5 | 5 |
| Hydrogen concentration used [mole $H_2$ per mole of glucose used] | 100 | 100 |
| Residence time in reactor [seconds, s] | 300 | 300 |
| Temperature in reactor [° C.] | 225 | 250 |
| Reactor in reactor [bar] | 250 | 250 |
| Mass flows in reactor: | | |
| a) total mass flow [kg/h] | 0.912 | 0.880 |
| b) water mass flow [ml/min] | 12.180 | 11.748 |
| c) 30% glucose mass flow [ml/min] | 2.286 | 2.206 |
| d) hydrogen mass flow [ml/min] | 28.166 | 27.168 |
| pH-Value | 6 | 6 |

As in example 1 and for performing experiments E5 and E6, the reactor containing the hydrogenating catalyst in the form of the fixed bed is started up by being supplied with a clean water flow at the reaction pressure of 250 bar and the reaction temperature of 225° or 250° C. On reaching a constant water flow under the indicated pressure and temperature conditions, a hydrogen flow is supplied to the reactor in order to reduce and therefore activate the hydrogenating catalyst. On setting a constant water flow and constant hydrogen flow with the value given in table 3, the 30% glucose solution is added and the mass glucose flow indicated in table 3 is set. In the present embodiment the glucose concentration in the reactor is set using dosing pumps in such a way that a value of 5 mass %, based on the total mass flow added to the reactor is obtained. By a corresponding control of the associated dosing pump it is possible to set the residence time of 300 or 5 min, whilst taking account of the density of the medium under the conditions prevailing in the reactor and the given volume flow.

The following table 4 summarizes the results obtained from the experiments on the basis of the conversion of the glucose used as the educt and with the yields of the sugar alcohols sorbitol, mannitol and further polyalcohols obtained as products.

TABLE 4

| Experiment | E5 | E6 |
|---|---|---|
| Carbon recovery rate ($TOC_{products}$[1]/$TOC_{educts}$[1] in [%]) | 76 | 59 |
| Glucose conversion [%] | 100 | 100 |
| Sorbitol yield[2] [%] | 35 | 11 |
| Mannitol yield[2] [%] | 18 | 12 |
| $C_6$-alcohol yield [%] | <9 | <3 |
| $C_3$-/$C_4$-alcohol yield [%] | <25 | <34 |

As is apparent from table 4, the yield of further polyols, particularly $C_3$ and $C_4$ polyalcohols, compared with the sorbitol can be increased by raising the temperature to a value of approximately 225° or 250° C. Whereas at 225° C. (E5) there is a sorbitol to mannitol product ratio of approximately 1:2, without any caramelization of the glucose used due to the inventively very short residence time in the reactor, there is an increase in the proportion of $C_3$ and $C_4$ polyalcohols, which substantially completely comprise $C_3$ polyalcohols 1,3-propanediol and propanetriol (glycerin) and $C_4$ polyalcohols 2,3-butanediol and 1,4-butanediol, to approximately 25%, based on the total product quantity. The proportion of other polyalcohols, differing from sorbitol and mannitol, is below 10%.

In the case of a reaction temperature of 250° C. (E6), the sorbitol to mannitol product ratio is approximately 1:1 and in particular the sorbitol proportion decreases with increasing temperature. There is an increased $C_3$ and $C_4$ polyalcohol yield to approximately one third of the total product quantity and once again virtually exclusively 1,3-propanediol and propanetriol (glycerin), as well as 2,3-butanediol and 1,4-butanediol are obtained. The proportion of other $C_6$ alcohols, differing from sorbitol and mannitol, drops to approximately 3%.

Also at temperatures of 225° and 250° C., there is a complete conversion of the glucose used of 100%. An advantageous hydrogen concentration is once again approximately 10 to 200 mole hydrogen per mole of glucose used and preferably between approximately 20 and 150 mole hydrogen per mole of glucose used.

Example 3

Continuous production of the sugar alcohols sorbitol and mannitol and further polyalcohols by hydrogenating glucose in aqueous solution with gaseous hydrogen in the presence of a ruthenium/ruthenium oxide mixed catalyst on aluminium oxide in the form of a fixed bed introduced into the reactor.

The monosaccharide glucose as the educt in aqueous solution with gaseous hydrogen is continuously reacted in the high quality steel tubular reactor having a length of twice 163 cm (connected in parallel) and an internal diameter of 9 mm according to examples 1 and 2. The tubular reactor contains a fixed bed of a ruthenium/ruthenium oxide mixed catalyst on particles of aluminium oxide as the carrier. The experiment is performed at a temperature of 200° C. and a residence time of 300 s, but with different hydrogen and glucose concentrations, the parameters summarized in the following table 5 being set.

TABLE 5

| Experiment | E7 | E8 | E9 | E10 |
|---|---|---|---|---|
| Glucose concentration in reactor (glucose mass-% in total reactor mass flow) | 5 | 2 | 1 | 2 |
| Hydrogen concentration used (mole $H_2$/mole glucose used) | 100 | 500 | 1000 | 1000 |
| Residence time in reactor [seconds, s] | 300 | 300 | 300 | 300 |
| Temperature in reactor [° C.] | 200 | 200 | 200 | 200 |
| Pressure in reactor [bar] | 250 | 250 | 250 | 250 |

According to examples 1 and 2, for performing experiments E7 to E10, the reactor is started up with the hydrogenating catalyst in the form of a fixed bed contained therein, by supplying the reactor with a flow of clean water at the reaction pressure of 250 bar and reaction temperature of 200° C. On reaching a constant water flow under the indicated pressure and temperature conditions, a hydrogen flow is supplied to the reactor in order to reduce and therefore activate the hydrogenating catalyst. On setting a constant water flow and a constant hydrogen flow with the value given in table 5 in each case, the glucose solution is added and the mass glucose flow indicated in table 5 is set. The glucose concentration in the reactor in the present embodiment is so set by using dosing pumps that there is a value between 1 and 5 mass %, based on the total mass flow added to the reactor. The residence time of 300 s or 5 min can also be set by corresponding control of the associated dosing pump, whilst taking account of the density of the medium under the conditions prevailing in the reactor and the given volume flow.

Table 6 gives the results obtained in the experiments on the basis of the yield of the glucose used as the educt and with the aid of the yields of the sugar alcohols sorbitol, mannitol and further polyalcohols obtained as products.

TABLE 6

| Experiment | E7 | E8 | E9 | E10 |
|---|---|---|---|---|
| Carbon recovery rate ($TOC_{products}^{1)}/TOC_{educts}^{1)}$ in [%]) | 93 | 68 | 99 | 80 |
| Glucose conversion [%] | 100 | 100 | 100 | 100 |
| Sorbitol yield[2)] [%] | 11.1 | 17.4 | 16.9 | 9.4 |
| Mannitol yield[2)] [%] | 12.6 | 8.5 | 6.9 | 6.8 |
| $C_6$-alcohol yield [%] | 6.4 | — | — | — |
| $C_3$-/$C_4$-alcohol yield [%] | 27 | 36 | 49 | 33 |

The $C_3/C_4$ alcohols obtained with a yield of 49% in experiment E9 are investigated for the specific representatives thereof and the following composition was obtained (in each case expressed as the yield[2]) of the given polyalcohol):

| | |
|---|---|
| propanetriol (glycerin): | 9.2% |
| 1,3-propanediol: | 10.6% |
| 2,3-butanediol: | 19.6% |
| 1,4-butanediol: | 9.4%. |

As can be seen in table 6, as a function of the concentration of the glucose or hydrogen used in the reactor, under the indicated process parameters sorbitol and mannitol yields of up to approximately 24%, based on the total product quantity, and yields of polyols from the group propanetriol (glycerin), 1,3-propanediol, 2,3-butanediol, 1,4-butanediol and, in the case of experiment E7, further $C_6$ polyols (not further defined) of in all up to approximately 50%, based on the total product quantity can be obtained, by setting a hydrogen concentration higher than in example 2, here between 100 and 1000 mole/$H_2$ mole of glucose used. Once again there is a complete conversion of the glucose used in all experiments.

The product range of the polyalcohols according to experiment E9 was used for producing polyurethane testpieces by polymerization and the aforementioned results given in the attached drawing (curve A) were obtained.

Example 4

Continuous production of the sugar alcohols sorbitol and mannitol and further polyalcohols by hydrogenating glucose in aqueous solution with gaseous hydrogen in the presence of a ruthenium/ruthenium oxide mixed catalyst on aluminium oxide in the form of a fixed bed introduced into the reactor.

The monosaccharide glucose as the educt in aqueous solution with gaseous hydrogen is continuously reacted in the high quality steel tubular reactor with a length of twice 163 cm (connected in parallel) and with an internal diameter of 9 mm in accordance with examples 1 to 3. The tubular reactor contains a fixed bed of a ruthenium/ruthenium oxide mixed catalyst on particles of aluminium oxide as the carrier. The experiment is performed under a constant temperature of 220° C. and a constant hydrogen or glucose concentration, but with different residence times of 150 s (experiment E11) and 300 s (experiment E12), the parameters summarized in the following table 7 being set.

TABLE 7

| Experiment | E11 | E12 |
|---|---|---|
| Glucose concentration in reactor (glucose mass-% in total reactor mass flow) | 5 | 5 |

TABLE 7-continued

| Experiment | E11 | E12 |
|---|---|---|
| Hydrogen concentration used (mole $H_2$/mole glucose used) | 100 | 100 |
| Residence time in reactor (seconds, s) | 150 | 300 |
| Temperature in reactor [° C.] | 220 | 220 |
| Pressure in reactor [bar] | 250 | 250 |

Experiments E11 and E12 are performed in accordance with examples 1 to 3, whilst taking account of the aforementioned process parameters.

The results obtained in experiments E11 and E12 are summarized in the following table 8 with the aid of the conversion of the glucose used as the educt and the yields of the sugar alcohols sorbitol, mannitol and further polyalcohols obtained as products.

TABLE 8

| Experiment | E11 | E12 |
|---|---|---|
| Carbon recovery rate ($TOC_{products}^{1)}/TOC_{educts}^{1)}$ in [%]) | 82 | 65 |
| Glucose conversion [%] | 100 | 100 |
| Sorbitol yield[2)] [%] | 12.4 | 3.0 |
| Mannitol yield[2)] [%] | 13.2 | 7.0 |
| $C_6$-alcohol yield [%] | 6.3 | 2.8 |
| $C_3$-/$C_4$-alcohol yield [%] | 26 | 10 |

As can be gathered from table 8, with a reactor temperature of 220° C. the yields of further polyols, particularly the presently measured $C_3/C_4$ polyols propanetriol (glycerin), 1,3-propanediol, 2,3-butanediol and 1,4-butanediol and also the not further defined $C_6$ polyols are not increased by lengthening the residence time under otherwise constant process parameters, but instead a doubling of the residence time from 150 to 300 s under the indicated process parameters leads to a reduction by more than half of the yields of said polyols. There is also a reduction by approximately half of the yield of the sugar alcohols sorbitol and mannitol under a substantially constant ratio of approximately 2:1 to 2.5:1. In both cases a complete conversion of the glucose used is obtained.

Example 5

Continuous production of the sugar alcohols sorbitol and mannitol, as well as further polyalcohols by hydrogenating glucose in aqueous solution with gaseous hydrogen in the presence of a ruthenium/ruthenium oxide mixed catalyst on aluminium oxide in the form of a fixed bed introduced into the reactor.

The monosaccharide glucose as the educt in aqueous solution with gaseous hydrogen is continuously reacted in the high quality steel tubular reactor with a length of twice 163 cm (connected in parallel) and an internal diameter of 9 mm in accordance with examples 1 to 4. The tubular reactor contains a fixed bed of a ruthenium/ruthenium oxide mixed catalyst on particles of aluminium oxide as the carrier. The experiment is performed four times with a residence time of 5 s and at 250°, 300°, 350° and 400° C. with a glucose concentration of 5 mass % and a hydrogen concentration of 100 mole $H_2$/mole of glucose used in the reactor. The following table 9 lists the set parameters.

TABLE 9

| Experiment | E13 | E14 | E15 | E16 |
|---|---|---|---|---|
| Glucose concentration in reactor (Glucose mass % in total reactor mass flow) | 5 | 5 | 5 | 5 |
| Hydrogen concentration used (mole $H_2$ mole glucose used) | 100 | 100 | 100 | 100 |
| Residence time in reactor [seconds, s] | 5 | 5 | 5 | 5 |
| Temperature in reactor [° C.] | 250 | 300 | 350 | 400 |
| Pressure in reactor [bar] | 250 | 250 | 250 | 250 |

Experiments E13 to E16 are performed in accordance with examples 1 to 4, whilst taking account of the aforementioned process parameters.

Table 10 gives the results obtained during the experiments on the basis of the conversion of the glucose used as the educt and the yields of the sugar alcohols sorbitol, mannitol and further polyalcohols obtained as products.

TABLE 10

| Experiment | E13 | E14 | E15 | E16 |
|---|---|---|---|---|
| Carbon recovery rate ($TOC_{products}$[1]/$TOC_{educts}$[1] in [%]) | 83 | 80 | 54 | 20 |
| Glucose conversion [%] | 84 | 80 | 54 | 20 |
| Sorbitol yield[2] [%] | 41.8 | 11.0 | 1.0 | 0.1 |
| Mannitol yield[2] [%] | 6 | 4.2 | 0 | 0 |
| $C_2$-alcohol yield [%] | — | 17.2 | 4.9 | 2.0 |
| $C_3$-/$C_4$-alcohol yield [%] | 13 | 29.5 | 13 | 6.5 |

Note: As the $C_2$ alcohol ethanediol with the yields given in table 10 was determined. As $C_3$/$C_4$ alcohols were determined the sums of the yields given in table 10 for propanetriol (glycerin), 1,3-propanediol, 2,3-butanediol and 1,4-butanediol.

It is clear from experiments E13 to E16 that an increase in the reaction temperature to above 300° C. does not lead to a rise in the yield of shorter-chain polyols, but instead the yield thereof decreases, accompanied by a decreasing conversion of the glucose used. Despite the very short residence time of 5 s, at 250° C. (E13) there is still a sorbitol yield of approximately 42% and a mannitol yield of 6%, whilst approximately 13% polyols from the group propanetriol (glycerin), 1,3-propanediol, 2,3-butanediol and 1,4-butanediol were obtained. At 300° C. (E14) there is a sorbitol/mannitol yield of only 11 or approximately 4%, whereas the yield of the indicated polyols increases to approximately 30%. There is also a maximum ethanediol yield of approximately 17%. With higher temperatures of 350° and 400° C. (E15 and E16), there is a drastic decrease in the yields of all the desired products.

Example 6

Continuous production of the sugar alcohols sorbitol and mannitol and optionally further polyalcohols by hydrogenating fructose in aqueous solution with gaseous hydrogen in the presence of a ruthenium/ruthenium oxide mixed catalyst an aluminium oxide in the form of a fixed bed introduced into the reactor.

The monosaccharide fructose as the educt in aqueous solution with gaseous hydrogen is continuously reacted in the high quality steel tubular reactor with a length of twice 163 cm (connected in parallel), with an internal diameter of 9 mm in accordance with examples 1 to 5. The tubular reactor contains a fixed bed of a ruthenium/ruthenium oxide mixed catalyst on particles of aluminium oxide as the carrier. The experiment is performed three times in each case at 150° C. and in each case twice a fructose concentration of 20 mass % (experiments E17 and E18) and once a fructose concentration of 1 mass % (experiment E19), in each case based on the total mass flow in the reactor is set. The set parameters are listed in the following table 11.

TABLE 11

| Experiment | E17 | E18 | E19 |
|---|---|---|---|
| Fructose concentration in reactor (fructose mass % in total reactor mass flow) | 20 | 20 | 1 |
| Hydrogen concentratioin used (mole $H_2$/mole fructose used) | 25 | 25 | 100 |
| Residence time in reactor [seconds, s] | 300 | 300 | 300 |
| Temperature in reactor [° C.] | 150 | 150 | 150 |
| Pressure in reactor [bar] | 250 | 250 | 250 |

For performing experiments E17 to E19 the reactor with the hydrogenating catalyst contained therein in the form of a fixed bed is firstly started up by supplying the reactor with a clean water flow under the reaction pressure of 250 bar and reaction temperature of 150° C. On attaining a constant water flow under the indicated pressure and temperature conditions, a hydrogen flow is supplied to the reactor in order to reduce and therefore activate the hydrogenating catalyst. On setting a constant water flow and a constant hydrogen flow with the particular value given in table 11, the fructose solution is added and in each case the fructose mass flow indicated in table 5 is set. The fructose concentration in the reactor is so adjusted by using dosing pumps that there is a value of 20 (experiments E17 and E18) or 1 mass % (experiment E19), based on the total mass flow added to the reactor. The residence time of 300 s or 5 min can also be set by a corresponding control of the associated dosing pump, whilst taking account of the density of the medium under the conditions prevailing in the reactor and the given volume flow.

The following table 12 gives the results obtained in the experiments on the basis of the conversion of the fructose used as the educt and the yields of the sugar alcohols sorbitol, mannitol and further polyalcohols obtained as products.

TABLE 12

| Experiment | E17 | E18 | E19 |
|---|---|---|---|
| Carbon recovery rate ($TOC_{products}$[1]/$TOC_{educts}$[1] in [%]) | 98 | 100 | 86.8 |
| Fructose conversion [%] | 100 | 100 | 100 |
| Sorbitol yield[2] [%] | 48.3 | 44.8 | 34.9 |
| Mannitol yield[2] [%] | 61.6 | 59.3 | 36.9 |
| $C_6$-alcohol yield [%] | <1 | <1 | <1 |
| $C_3$-/$C_4$-alcohol yield [%] | <1 | <1 | <1 |

Experiments E17 to E19 show that with a residence time of 300 s, a pressure of 250 bar and a temperature of 150° C. it is possible to obtain a complete fructose conversion of 100% in the case of continuous catalytic hydrogenation of the fructose with hydrogen in the presence of ruthenium/ruthenium oxide on aluminium oxide. There are approximately constant yields or selectivities of the sugar alcohols sorbitol and mannitol in a ratio of approximately 2:3, which also remains substantially constant on raising the temperature, unlike when using glucose as the educt (cf. examples 1 ff), whereas the proportion of the further reaction products, such as $C_3$, $C_4$ and $C_6$ alcohols, then rises.

With a set fructose concentration in the reactor of 1 mass % (experiment E19), there are slightly inferior mannitol and sorbitol yields compared with a fructose concentration in the reactor of 20 mass % (E17 and E18). An ideal range can be established between approximately 5 and approximately 40 mass % fructose, based on the total mass flow in the reactor.

Example 7

Continuous production of the sugar alcohols sorbitol and mannitol and optionally further polyalcohols by hydrogenating saccharose (disaccharide with a glucose unit and a fructose unit) in aqueous solution with gaseous hydrogen in the presence of a ruthenium/ruthenium oxide mixed catalyst on aluminium oxide in the form of a fixed bed introduced into the reactor.

The disaccharide saccharose as the educt in aqueous solution with gaseous hydrogen is continuously reacted in the high quality steel tubular reactor with a length of twice 163 cm (connected in parallel) and an internal diameter of 9 mm according to examples 1 to 6. The tubular reactor contains a fixed bed of a ruthenium/ruthenium oxide mixed catalyst on particles of aluminium oxide as the carrier. The experiment is performed in all three times, i.e. once at 150° C. (E20), once at 200° C. (E21) and once at 250° C. (E22), the set test parameters being summarized in the following table 13.

TABLE 13

| Experiment | E20 | E21 | E22 |
|---|---|---|---|
| Saccharose concentration in reactor (Saccharose mass-% in total reactor mass flow) | 1 | 5 | 5 |
| Hydrogen concentration used (mole $H_2$/mole saccharose used) | 300 | 300 | 300 |
| Residence time in reactor [seconds, s] | 300 | 300 | 300 |
| Temperature in reactor [° C.] | 150 | 200 | 250 |
| Pressure in reactor [bar] | 250 | 250 | 250 |

For performing experiments E20 to E22 the reactor with the hydrogenating catalyst contained therein in the form of a fixed bed is firstly started up by supplying a clean water flow to the reactor under the reaction pressure of 250 bar and reaction temperature of 150°, 200° or 250° C. On attaining a constant water flow under the indicated pressure and temperature conditions, a hydrogen flow is also supplied to the reactor in order to reduce and therefore activate the hydrogenating catalyst. On setting a constant water flow and constant hydrogen flow with the values given in table 13, the saccharose solution is added and the saccharose mass flow indicated in table 13 is set. The saccharose concentration in the reactor is so adjusted by dosing pumps that there is a value of 5 (E21 and E22) and 1 mass % (E20), based on the total mass flow added to the reactor. The residence time of 300 s or 5 min can also be set by a corresponding control of the associated dosing pump, whilst taking account of the density of the medium under the conditions prevailing in the reactor and the given volume flow.

The following table 14 gives the results obtained in the experiments on the basis of the conversion of the saccharose used as the educt and the yields of the sugar alcohols sorbitol and mannitol obtained as products.

TABLE 14

| Experiment | E20 | E21 | E22 |
|---|---|---|---|
| Carbon recovery rate ($TOC_{products}$[1]/$TOC_{educts}$[1] in [%]) | 88 | 93 | 30 |
| Saccharose conversion [%] | 59 | 98 | 100 |
| Sorbitol yield[2] [%] | 49 | 64.5 | 5.1 |
| Mannitol yield[2] [%] | 18 | 35.5 | 6.2 |

Experiments E20 to E22 show that with a residence time of 300 s, a pressure of 250 bar and a temperature of 200° and 250° C. (E21 and E22) it is possible to obtain a substantially complete saccharose conversion of 100% accompanied by continuous catalytic hydrogenation of the saccharose with hydrogen in the presence of ruthenium/ruthenium oxide on aluminium oxide. At a temperature of 150° C. and in the case of the disaccharide used in the form of saccharose, when compared with a temperature of 200° C. there are inferior sorbitol and mannitol yields and a conversion of only roughly 60%, which is probably due to the fact that at this temperature the saccharose had not completely split into glucose and fructose. This applies both for a saccharose concentration i the reactor of 1 mass %, as in experiment E20, and for a saccharose concentration of 5 mass % in the reactor according to experiments E21 and E22 (not reproduced in detail, but in each case based on the total mass flow). An optimum parameter range for the temperature in the case of a desired product in the form of sorbitol and mannitol is between approximately 175° C. and approximately 225° C., particularly approximately 200° C. (E21).

In the indicated temperature range there are yields of the sugar alcohols sorbitol and mannitol, here in a ratio between approximately 3:1 and 2:1, the product ratio being displaced in the direction of mannitol with rising temperature. On raising the temperature to 250° C. (E22), the proportion of the here not reproduced, further reaction products, such as $C_3$, $C_4$ and $C_6$ alcohols, mainly 1,3-propanediol and propanetriol (glycerin) and 2,3-butanediol and 1,4-butanediol rises significantly. The sorbitol/mannitol yields are approximately only 5.1 and 6.2%.

SUMMARY

The process according to the invention makes it possible to effectively produce the sugar alcohols sorbitol and mannitol by means of an easily handleable catalyst active over very long time periods, in the case of very short reaction times and a complete conversion of the educts, whilst ensuring easy settability and adjustability of the desired product range mannitol and sorbitol, whilst also permitting an effective production of further polyols, particularly from the group propanetriol (glycerin), 1,3-propanediol, 2,3-butanediol and 1,4-butanediol, as well as ethanediol from regrowing raw materials. Compared with polyurethanes produced from corresponding polyols obtained from petroleum/natural gas, the polyurethanes produced can have improved material characteristics.

We claim:

1. A method for the production of polyalcohols in the form of sugar alcohols from the group sorbitol and/or mannitol and optionally further $C_6$ and/or $C_4$ and/or $C_3$ and/or $C_2$ polyols, the method comprising the step of:
   continuously reacting at least one mono-, di-, oligo- and/or polysaccharide containing at least one glucose and/or at least one fructose unit in the presence of a hydrogenating catalyst being ruthenium (Ru) and/or ruthenium oxide in aqueous phase, at elevated temperature and elevated pressure with hydrogen, to obtaining the polyols, wherein the temperature is between 120° and 280° C., the pressure at least 150 bar, and a dwell time of the reactants during catalytic hydrogenation is at most 400 s, the temperature, pressure and dwell time being adjusted to effect at least 98% educt conversion.

2. The method of claim 1, wherein the dwell time is 5 to 360 s.

3. The method of claim 1, wherein the pressure is at least 200 bar.

4. The method of claim 1, wherein product proportions of the sorbitol and mannitol sugar alcohols and/or the $C_6$ and/or $C_4$ and/or $C_3$ and/or $C_2$ polyols are affected by varying the setting of at least one of the temperature, the pressure, the dwell time, and/or hydrogen or educt concentration.

5. The method of claim 1, wherein an educt is glucose and/or fructose and/or a di-, oligo- or polysaccharide containing at least one glucose unit and also at least one fructose unit, saccharose and/or raffinose.

6. The method of claim 1, wherein an educt concentration is between 1 and 50 mass %, based on a total flow.

7. The method of claim 1, wherein the catalyst is mixed ruthenium/ruthenium oxide.

8. The method of claim 1, wherein the catalyst is immobilized on at least one carrier.

9. The method of claim 8, wherein the catalyst carrier is aluminium oxide ($Al_2O_3$).

10. The method of claim 3, wherein the pressure is at least 220 bar.

11. The method of claim 6, wherein an educt concentration is between 2 and 40 mass %, based on the total flow.

* * * * *